United States Patent
Borysewicz et al.

(10) Patent No.: US 8,778,817 B2
(45) Date of Patent: Jul. 15, 2014

(54) METHOD OF MAKING A COVER MATERIAL INCLUDING A SKIN CARE COMPOSITION

(75) Inventors: Krystyna M. Borysewicz, Old Bridge, NJ (US); Ricky Ray Burrow, Doylestown, PA (US); Jenny G. Du, Weston, FL (US); Joseph Michael Luizzi, Newtown, PA (US); Maria Cristina Niciporciukas, Long Valley, NJ (US); Kenneth A. Pelley, Hopewell, NJ (US); John Poccia, Monmouth Beach, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 1912 days.

(21) Appl. No.: 11/589,590

(22) Filed: Oct. 30, 2006

(65) Prior Publication Data

US 2008/0102722 A1 May 1, 2008

(51) Int. Cl.
*D04H 1/44* (2006.01)

(52) U.S. Cl.
USPC ............................................. 442/123; 604/359

(58) Field of Classification Search
USPC .................................. 604/378, 359; 442/123
See application file for complete search history.

(56) References Cited

U.S. PATENT DOCUMENTS

| | | | |
|---|---|---|---|
| 3,510,005 A | | 5/1970 | Butler et al. |
| 5,437,653 A | * | 8/1995 | Gilman et al. ................ 604/378 |
| 5,560,878 A | * | 10/1996 | Dragoo et al. ................ 264/115 |
| 5,874,164 A | * | 2/1999 | Caldwell ..................... 428/306.6 |
| 6,296,862 B1 | * | 10/2001 | Paul et al. ..................... 424/402 |
| 6,579,274 B1 | | 6/2003 | Morman |
| 6,689,932 B2 | * | 2/2004 | Kruchoski et al. ............. 604/360 |
| 7,462,756 B2 | * | 12/2008 | Malowaniec ................. 604/381 |
| 2002/0103469 A1 | | 8/2002 | Chen et al. |
| 2004/0116018 A1 | * | 6/2004 | Fenwick et al. .............. 442/164 |
| 2004/0214495 A1 | | 10/2004 | Foss |
| 2004/0242097 A1 | * | 12/2004 | Hasenoehrl et al. ............ 442/59 |
| 2005/0136098 A1 | | 6/2005 | Spadini |
| 2006/0084344 A1 | * | 4/2006 | Bonneh ......................... 442/382 |

FOREIGN PATENT DOCUMENTS

| | | |
|---|---|---|
| DE | 10037862 | 2/2002 |
| WO | WO 93/06924 A | 4/1993 |
| WO | 2005/042041 | 5/2005 |

OTHER PUBLICATIONS

Product data obtained from alibaba.com used as evidentiary reference only. copyright 1999-2009.*

* cited by examiner

*Primary Examiner* — Suzanne Ziska

(57) ABSTRACT

A method of making a cover material for an absorbent article including the steps of providing a fibrous nonwoven substrate, the substrate having a tortuousity value in the range of about 0.8 to about 3.0, applying a particulate skin care material to the substrate, the particulate skin care comprising a particulate material having a particle size in the range of about 1 micron to about 75 microns, and applying a compressive force to the substrate to impregnate the substrate with the particulate skin care material.

30 Claims, 2 Drawing Sheets

METHOD OF MAKING A COVER MATERIAL INCLUDING A SKIN CARE COMPOSITION

FIELD OF THE INVENTION

The present invention relates to method of making a cover material for absorbent articles including a skin care material that it is readily transferable to the skin during use and a method of making said cover material.

BACKGROUND OF THE INVENTION

Many types of disposable absorbent products, such as sanitary napkins, panty liners and the like are commercially available that have a high capacity for absorbing body exudates, such as menses. Absorbent articles of this type typically include a liquid pervious topsheet, an absorbent core, and a liquid impervious backsheet. Although these articles are effective at absorbing fluid it is known that the skin located directly underneath the article is more susceptible to skin disorders such as erthema, heat rash, pressure marks and other minor skin inflammations. This irritation and/or inflammation results from extended contact with the menses, urine or both. In addition, absorbent articles of this type are generally worn for extended periods of time and as such do not permit the skin to ventilate in efficient manner which also contributes to skin irritation.

In view of the above, substantial efforts have been made to provide skin care compositions on the body-facing surface of disposable absorbent articles. These efforts have been focused on the cover materials of such articles because the cover material typically has the greatest contact with the skin. Further, the benefits obtained by such skin care compositions are often only realized if the skin care material is transferred to the skin of the wearer.

The skin care compositions used on known absorbent articles generally fall within one of three categories: (1) compositions that are essentially dry particulate materials at room temperature, are dry to the touch, and do not undergo a phase change at "elevated temperatures"; (2) compositions that are essentially liquids at room temperature, are wet to the touch, and/or compositions that undergo a phase change at an elevated temperature, enabling the application of the skin care material in an essentially liquid form at either room temperature or an elevated temperature; and (3) suspensions or solutions that are combinations of (1) and (2). "Elevated temperatures" as used herein mean a temperature in the range from about 0° C. to about 150° C.

Those absorbent articles that include essentially liquid skin care compositions have the disadvantage that it can be difficult to apply the material to the absorbent article at the high manufacturing speeds employed during the manufacture of disposable absorbent articles. In addition, absorbent articles having an essentially liquid skin care material applied to a body facing surface thereof also often have a sticky feel during use that users find uncomfortable. Further, essentially liquid skin care compositions may also interfere with the absorbency of the article.

Absorbent articles that employ essentially dry particulate skin care compositions have other disadvantages. In particular it has been found that during the manufacture of such absorbent articles the skin care material cannot be effectively retained in the article during manufacture causing the material to be prematurely released. This premature release can cause problems during manufacture and also limits the efficacy of the skin care material in the final product. To overcome this problem, immobilizing agents such as emollients or waxes may be employed to assist in securing the particulate material to the surface of the absorbent article. However, such immobilizing agents present many of the same problems discussed above with respect to liquid skin care compositions. Further, the use of immobilizing agents may also prevent the effective transfer of the skin care material to body during use of the article.

In view of the above there is a need for a cover material for use in absorbent articles that includes an essentially dry particulate skin care material that can be utilized in the manufacture of disposable absorbent articles, and at the speeds required during the manufacture of such absorbent articles. There is also a need for such a cover material that effectively retains the essentially dry particulate skin care material in place during manufacture without the use of an immobilizing agent yet also releases the skin care material during use of the absorbent article.

SUMMARY OF THE INVENTION

In view of the foregoing, the present invention provides, according to a first aspect of the invention, a method of making a cover material for an absorbent article including the steps of providing a fibrous nonwoven substrate, the substrate having a tortuousity value in the range of about 0.8 to about 3.0, conveying the substrate in a machine direction to means for applying a skin care composition, applying a particulate skin care material to the substrate, the particulate skin care comprising a particulate material having a particle size in the range of about 1 micron to about 75 microns, conveying the substrate to means for applying a compressive force to the substrate, applying a compressive force to the substrate to impregnate the substrate with the particulate skin care material.

BRIEF DESCRIPTION OF THE DRAWINGS

Examples of embodiments of the present invention will now be described with reference to the drawings, in which.

DETAILED DESCRIPTION OF THE INVENTION

Figure 1:
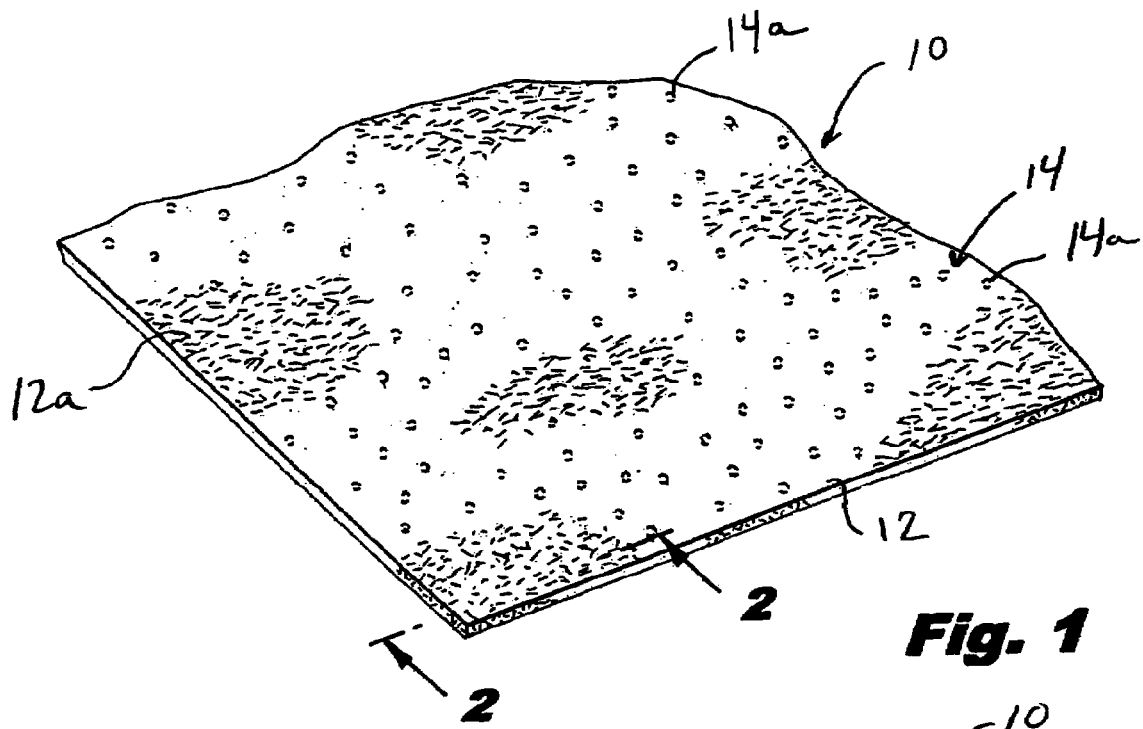
FIG. 1 is a perspective view of a cover material for an absorbent article in accordance with the present invention.
Figure 2:
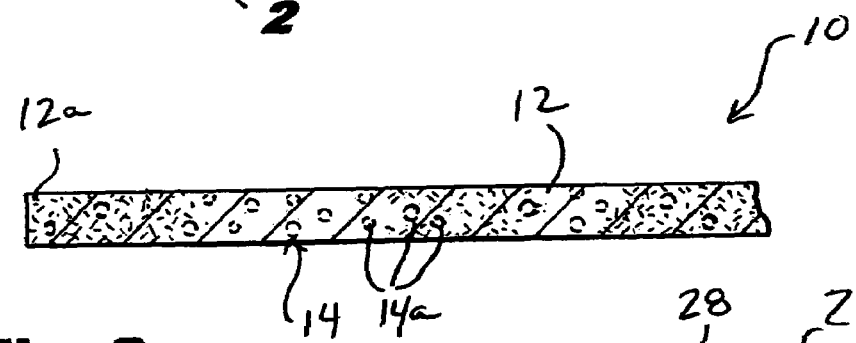
FIG. 2 is a sectional view of the cover material shown in FIG. 1 taken along line 2-2 thereof.

Referring to FIGS. 1 and 2, there is shown according to a first aspect of the invention, a cover material 10 for an absorbent article. The cover material 10 includes a fibrous nonwoven substrate 12 and a particulate skin care material 14 that is formed from a particulate material comprising a plurality of individual particles 14a. As shown in FIG. 1 and FIG. 2, the substrate 12 is a fibrous material, preferably a fibrous nonwoven material including a plurality of fibers 12a, and is impregnated with the particulate skin care material 14. In one embodiment of the invention, the particulate skin care material 14 consists of, or alternatively consists essentially of, a plurality of individual particles 14a.

Figure 3:
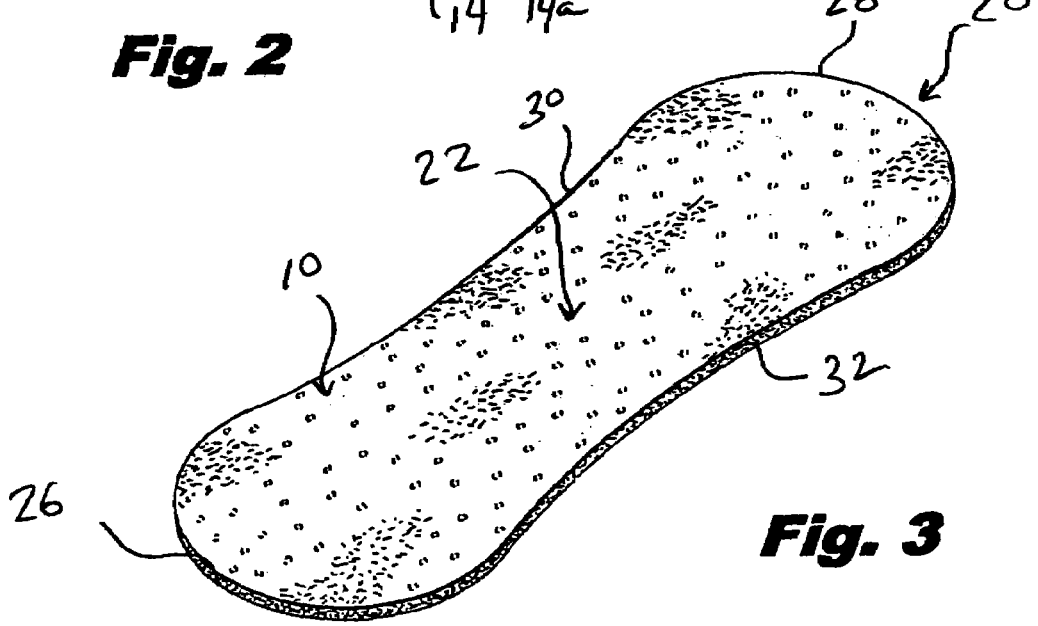
FIG. 3 is a perspective view of a pantiliner in accordance with the present invention including the cover material shown in FIG. 1.
Figure 4:
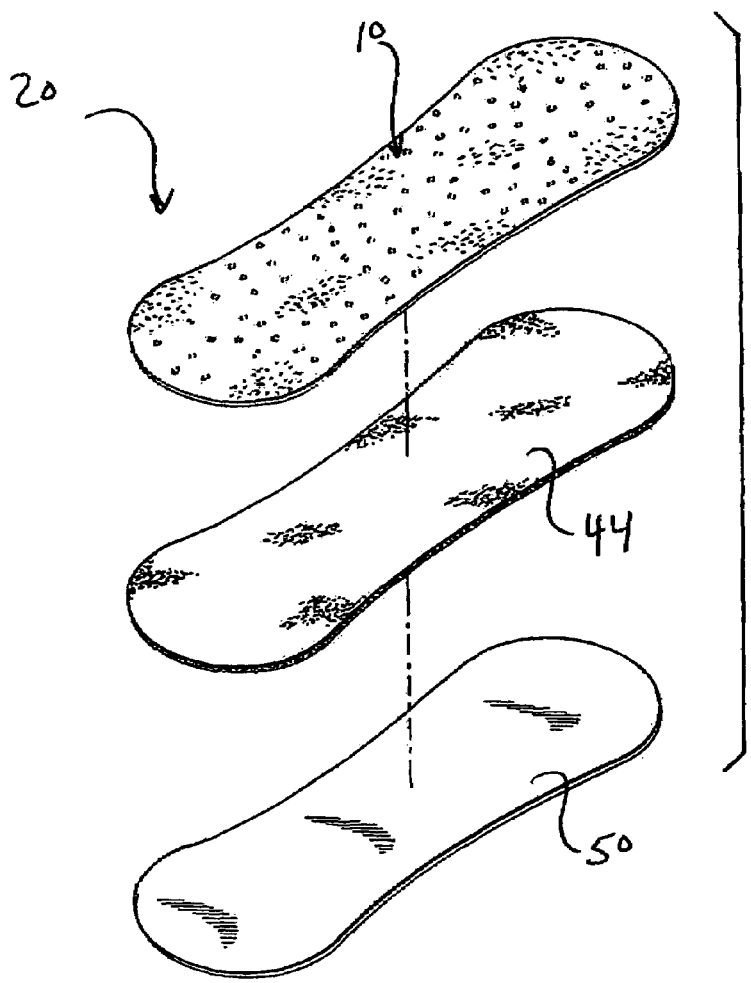
FIG. 4 is an exploded view of the pantiliner shown in FIG. 3.

Referring to FIGS. 3 and 4, there is shown according to a second aspect of the invention, a pantiliner 20 including the cover material 10. In the particular embodiment shown in FIGS. 3 and 4, the present invention is depicted as a pantiliner 20 but the present invention also includes other sanitary absorbent articles such sanitary napkins, diapers, adult incontinence articles and like.

The pantiliner 20 has a main body 22 with a first transverse side 26 defining a front portion thereof and a second transverse side 28 defining a rear portion thereof. The main body also has two longitudinal sides, namely a longitudinal side 30 and a longitudinal side 32.

As depicted in FIG. 4, the main body 22 is of a laminate construction and includes the inventive fluid-permeable cover layer 10, described in detail below, a fluid-impervious barrier layer 50, and an optional absorbent system 44 arranged between the cover layer 10 and the barrier 50. The absorbent system 44 may comprise a single layer of material or may comprise multiple layers. For example, the absorbent system may comprise a single layer core or it may include a transfer layer and a core.

Cover Layer

As show in FIGS. 1 and 2, the cover material 10 according to the present invention includes a fibrous nonwoven substrate 12 and a particulate skin care material 14 that is formed from a particulate material comprising a plurality of individual particles 14a. As shown in FIG. 1 and FIG. 2, the substrate 12 is a fibrous material, preferably a fibrous nonwoven material including a plurality of fibers 12a, and is impregnated with the particulate skin care material 14.

"Particulate skin care material" as used herein means a material that includes a plurality of distinct particulate elements, and said particulate elements are not suspended in liquid or dissolved as a solution in liquid at room temperature. In addition such particulate material does not undergo a phase change at an "elevated temperature." "Elevated temperature" as used herein means a temperature in the range from about 0° C. to about 150° C. Examples of particulate skin care materials include organic and inorganic powders such as cornstarch, aloe powder, talc, kaolin, sericite, mica, calcium carbonate, magnesium carbonate, silicic anhydride, zinc oxide, titanium oxide, and tribasic-calcium phosphate.

The substrate 12 may be a relatively low density, bulky, high-loft non-woven web material. The substrate 12 may be composed of only one type of fiber, such as polyester, polypropylene, or rayon, or it may include a mixture of more than one fiber. The substrate 12 may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof.

Bi-component fibers may be made up of a polyester layer and a a polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer may be mounted to the absorbent layer and/or to the barrier layer.

Advantageously, the fibers which make up the substrate 12 should not lose their physical properties when they are wetted, in other words they should not collapse or lose their resiliency when subjected to water or body fluid. The substrate 12 may be treated to allow fluid to pass through it readily. The cover 10 also functions to transfer the fluid quickly to the other layers of the absorbent system 44. Thus, the substrate 12 is advantageously wettable, hydrophilic and porous. When composed of synthetic hydrophobic fibers such as polyester or bi-component fibers, the substrate 12 may be treated with a surfactant to impart the desired degree of wettability.

The substrate 12 may be manufactured using any one of a number of known nonwoven manufacturing techniques including spunlace, spunbond, thermalbond, hot through air bonding and latex bonding.

The cover layer 10 may be embossed to the remainder of the absorbent system 44 in order to aid in promoting hydrophilicity by fusing the cover to the next layer. Such fusion may be effected locally, at a plurality of sites or over the entire contact surface of cover layer 10 and absorbent system 44. Alternatively, the cover layer 10 may be attached to the absorbent system 44 by other means such as by adhesion.

In one embodiment of the invention, the substrate 12 is a a fibrous nonwoven material having a "tortuousity value" in the range of about 0.8 to about 3.0. In another embodiment of the present invention, the substrate 12 is a fibrous nonwoven material having a tortuosity value in the range of about 1.0 to about 1.8. It has been found that tortuousity values in the above ranges permit the substrate to effectively retain the particulate skin care material 14 during manufacture yet also effectively transfers the skin care material 14 to the skin during use.

"Tortuousity value (T)" as used herein is a dimensionless value that can be calculated according to the following formula:

$$T = Fr^* (Fd/Sd - 1)/Sp; \text{ where}$$

Fr=Fiber Radius in microns (microns);
Fd=Fiber Density in grams per meter cubed (g/m$^3$);
Sd=Substrate Density (g/m$^3$); and
Sp=Average pore size of substrate in microns (microns).

Fiber radius (Fr, in microns) is calculated according to the following formula:

$$Fr \text{ (microns)} = [((Fs/10000 \text{ m})/Fd)/3.14]^{1/2} * 10^6; \text{ where}$$

Fs=Fiber size in dtex, (note: 1 dtex=1 g/10000 m); and
Fd=Fiber density in grams per meter cubed (g/m$^3$).

The above described formula for Tortuousity was derived from the formulas described in article by Cohen, "A Wet Pore-Size Model for Coverstock Fabrics", Book of Papers: The International Nonwoven Fabrics Conference, INDATEC'90, Association of the Nonwoven Fabrics Industry, pp. 317-330 (1990), herein incorporated by reference.

Fiber density (Fd, in g/m$^3$) for a particular fiber corresponds to the specific material that fiber is formed from. Fiber density is typically specified by the fiber manufacturer in the product specification for the particular fiber.

Fiber size (Fs, dtex) is typically specified by the fiber manufacturer in the product specification for the particular fiber.

Substrate Density (Sd, g/m$^3$) is determined by the following formula:

$$Sd \text{ (g/m}^3\text{)} = \text{Substrate Basis Weight (g/m}^2\text{)/Substrate Thickness (m)}$$

Average pore size of the substrate (Sp, microns) may be determined utilizing a suitable apparatus such as a TRI/Autoporosimeter™, available from TRI, Princeton, N.J. The instrument and the use thereof is described in the paper "Liquid Porosimetry: New Methodology and Applications" by Dr. B. Miller and Dr. I. Tyomkin, published in the Journal of Colloid and Interface Science, 162, 163-170, (1994). TRI/AC© PVD data treatment software was used for data evaluation.

If a single fiber is used to form the substrate then the above formula for fiber radius (Fr, in microns) holds and the calculated fiber radius may then be used in the tortuousity value formula (T) set forth above. However, if multiple fibers are used to form the substrate then an average fiber radius ($Fr_{ave}$) and an average fiber size $Fs_{ave}$ must be calculated. In order to determine the average fiber radius the average density of the fibers ($Fd_{ave}$) must first be calculated. For example, the average density of the fibers for a substrate containing two fibers can be calculated according to the following formula:

$$Fd_{ave} (g/m^3) = [Fd_1*W_1] + [Fd_2*W_2]; \text{ where}$$

$Fd_1$=density of the first fiber in g/m$^3$;
$W_1$=weight percent of first fiber;
$Fd_2$=density of the second fiber in g/m$^3$; and
$W_2$=weight percent of the second fiber.

In a similar fashion the average fiber size ($Fs_{ave}$) can be calculated as follows:

$$Fs_{ave} (dtex) = [Fs_1*W_1] + [Fs_2*W_2]; \text{ where}$$

$Fs_1$=size of the first fiber;
$W_1$=weight percent of first fiber;
$Fs_2$=size of the second fiber; and
$W_2$=weight percent of the second fiber.

An average fiber radius ($Fr_{ave}$) can then be calculated as follows:

$$Fr_{ave} (microns) = [((Fs_{ave}/10000 \text{ m})/Fd_{ave})/3.14]^{1/2} * 10^6$$

The "Tortuousity value (T)" can then be calculated according to the following formula:

$$T = Fr_{ave} * (Fd_{ave}/Sd - 1)/Sp$$

where
$Fr_{ave}$=Average Fiber Radius in microns (microns);
Fd=Average Fiber Density in grams per meter cubed (g/m$^3$);
Sd=Substrate Density (g/m$^3$); and
Sp=Average pore size of substrate in microns (microns).

In a one embodiment of the invention the fibrous nonwoven substrate 12 is free from any "immobilizing agents" for securing said particulate skin care material 14 to the substrate 12. "Immobilizing agent" as used herein means any material that functions to adhere the skin care material 14 to the substrate, and/or any material that functions to prevent the skin care material 14 from freely migrating within the substrate 12. Specific examples of immobilizing agents are disclosed in U.S. Pat. No. 6,570,054 to Gatto et al., the subject matter of which is hereby incorporated by reference.

As seen in FIG. 2, the substrate is preferably formed from a plurality of individual fibers 12a. In a one embodiment of the present invention the fibers 12a have a fiber density of about $5*10^5$ g/m$^3$ to about $2.0*10^6$ g/m$^3$. In another embodiment of the invention the fibers have a fiber density of about $9*10^5$ g/m$^3$ to about $1.5*10^6$ g/m$^3$. The "fiber density" for a particular fiber corresponds to the specific material that fiber is formed from, fiber density is typically specified by the fiber manufacturer in the product specification for the particular fiber.

In one embodiment of the invention, each of the fibers 12a have a fiber size (Fs) in the range of about 1.0 dtex to about 7.8 dtex. In another embodiment of the invention, each of said fibers 12 has a fiber size in the range of about 1.7 dtex to about 5.6 dtex. The fiber size is typically specified by the fiber manufacturer in the product specification for the particular fiber.

In one embodiment of the invention, each of the fibers 12a have a fiber radius in the range of about 3 microns to about 25 microns. In another embodiment of the invention, each of the fibers 12a have a fiber radius in the range of about 5 microns to about 12 microns.

An example of a suitable polyester fiber for use in the present invention is Wellman Type D203, 1.5 dpf (1.7 dtex), fiber length 38 mm, commercially available from Wellman, Inc., Charlotte, N.C. An example of a suitable rayon fiber for use in the present invention is Lenzing Type 8192, 1.5 dpf (1.7 dtex), fiber length 40 mm, commercially available from Lenzing AG, Lenzing, Austria.

In one embodiment of the invention the fibrous nonwoven substrate 12 has an average pore size in the range of about 40 microns to about 200 microns. In another embodiment the fibrous nonwoven substrate 12 has an average pore size in the range of about 60 microns to about 150 microns.

In one embodiment of the invention, the fibrous nonwoven substrate 12 has a basis weight in the range of about 40 gsm (g/m$^2$) to about 200 gsm, in another embodiment in the range of about 60 gsm to about 150 gsm.

In a one embodiment of the invention, the fibrous nonwoven substrate 12 has a density in the range of about $1.0*10^4$ g/m$^3$ to about $3.0*10^5$ g/m$^3$, and in another embodiment in the range of about $4.5*10^4$ g/m$^3$ to about $1.0*10^5$ g/m$^3$.

The cover material 10 according to the present invention also includes a particulate skin care material 14 composed of a particulate material comprising a plurality of individual particles 14a. In one embodiment of the invention, the particulate skin care material 14 consists of, or alternatively consists essentially of, a plurality of individual particles 14a.

"Particulate skin care material" as used herein means a material that includes a plurality of distinct particulate elements, and said particulate elements are not suspended in liquid or dissolved as a solution in liquid at room temperature. In addition such particulate material does not undergo a phase change at an elevated temperature. Examples of particulate skin care materials include organic and inorganic powders such as talk, kaolin, sericite, mica, calcium carbonate, magnesium carbonate, silicic anhydride, zinc oxide, titanium oxide, cornstarch, aloe powder, and tribasic-calcium phosphate, as well as combinations of these above materials. Examples of commercially available "particulate skin care materials" include cornstarch from Corn Products Corporation, Bedford Park, Ill., Zinc Oxide USP from Zinc Corporation of America, Monaca, Pa., and Tribasic calcium phosphate, NF from Rhone Poulenc, Chicago Heights, Ill.

In one embodiment of the invention each of the individual particles 14a has a particle size in the range of about 1 micron to about 75 microns, and the particles 14a have a moisture content of from about 3% to about 20%. In another embodiment of the invention each of the individual particles 14a have a particle size in the range of about 5 microns to about 30 microns and the particles 14a have a moisture content of from about 8% to about 14%. The particle size and moisture content for a specific particulate material is typically specified in the product specification for the particular material.

In one embodiment of the invention the particulate skin care material 14 is present in the nonwoven substrate 12 in an amount from about 1 gsm to about 50 gsm and in another embodiment in an amount from about 10 gsm to about 30 gsm.

Figure 5:
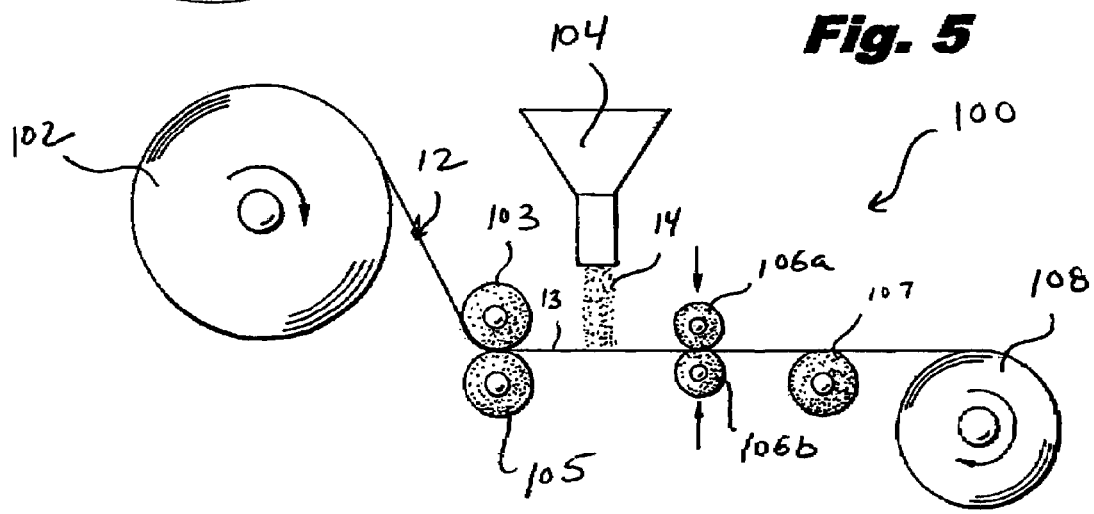
FIG. 5 is a schematic view of an apparatus for making the cover material shown in FIG. 1.

A method for making the cover material 10 according to the present invention will be described with reference to FIG. 5. FIG. 5 depicts an apparatus 100 for making the cover material 10 according to present invention, the apparatus 100 includes an unwind roll 102, means 104 for applying a particulate skin care material 14 to the nonwoven substrate 12, a pair of nip rolls 106a and 106b, and a rewind roll 108. The nip rolls 106a and 106b may have a smooth surface or may be provided with a pattern. The means 100 for applying the particulate skin care material 14 to the nonwoven substrate 12 may comprise any conventional means such as spray nozzles, gravity fed hopper, or the like.

During manufacture of the cover material 10, the substrate 12 is unwound from the unwind roll 102 and conveyed in a machine direction. The substrate 12 is conveyed in one embodiment of the invention at a speed in the range of about 7.5 m/min to about 500 m/min, and in another embodiment from about 100 m/min to about 350 m/min. The substrate 12 is conveyed over support rolls 103 and 105 to the means 104 for applying the particulate skin care material 14. The means 104 applies the particulate skin care material 14 to an upper surface 13 of the substrate 12. The substrate 12, and the skin care material 14, are then further conveyed in a machine direction to a pair of nip rolls 106a and 106b. In one embodiment of the invention, the nip rolls 106a and 106b function to apply a compressive force to the substrate In another embodiment of the invention, the nip rolls 106a and 106b are heated nip rolls and function to simultaneously apply a compressive force and heat to the substrate.

In one embodiment of the invention, the nip rolls 106a and 106b are arranged such that the surface of the rolls are in contact with one another, in other words the nip rolls 106a and 106b are arranged in a "zero gap" configuration. In this zero gap configuration a force is applied to rolls 106a and 106b in order to maintain the rolls in face to face contact. The specific amount of force required to maintain rolls 106a and 106b in face to face contact will vary somewhat depending upon certain variables such as the speed of the substrate 12 and the thickness of the substrate 12. Air cylinders or other means know to those skilled in the art may be used to apply the force required to maintain the rolls 106a and 106b in face to face contact.

It one embodiment, the compressive force applied to the substrate 12 is in the range from about 0.1 kN/cm to about 1.2 kN/cm (about 60 lbs/in to about 700 lbs/in), and in another embodiment from about 0.4 kN/cm to about 0.7 kN/cm (about 250 lbs/in to about 400 lbs/in). The applied force to the substrate expressed above is based upon the applied nip force divided by the width of the substrate.

In another embodiment of the invention, the nips rolls 106a and 106b are arranged such that there is a space between the surface of the rolls, i.e. the rolls are arranged in a "non-zero" gap configuration. In order for the rolls 106a and 106b to still apply a compressive force to the substrate, despite the "non-zero" gap configuration, the gap between the rolls must be less than a thickness ($S_t$) of the substrate 12. The gap setting, i.e. the distance between the faces of nip rolls 106a and 106b, will vary somewhat depending upon the particular substrate selected. However, it has been found that the gap setting (G), according to one embodiment, is selected such that it is greater than zero and less than one half the thickness of the substrate ($S_t$), and in another embodiment of the invention is in the range between from about 0.025 mm (0.001 inch) to about one quarter the thickness of the substrate. The gap setting (G) ranges in accordance with the invention, as recited above, can thus be expressed as follows:

0<G<0.5 $S_t$; or 0.025 mm<G<0.25 $S_t$ where $S_t$=Substrate Thickness

In order to maintain the gap setting between the nip rolls 106a and 106b it may be necessary to apply a nominal force to the rolls 106a and 106b merely to maintain the rolls in a constant position.

In the embodiment of the invention, wherein heat and a compressive force are simultaneously applied to the substrate 12, the surface of the nip rolls 106a and 106b in one embodiment of the invention are heated to a temperature in the range of from about about 25° C. to about 250° C. (77° F. to about 482° F.) and in another embodiment in the range from about 35° C. to about 150° C. (95° F. to about 300° F.). The temperature of the nip rolls 106a and 106b should be selected such that the nip rolls 106a and 106b do not melt the constituent fibers that form the substrate 12.

After the application of the compressive force, or the simultaneous application of the compressive force and heat, to the substrate 12, the substrate 12 is conveyed further over support roll 107 in a machine direction to the rewind roll 108. Alternatively the substrate may be conveyed further in the machine direction for further processing, for example incorporation into a pantiliner 20 of the type described herein.

Example of Inventive Cover Material

A specific example of a cover material 10 according to the present invention, and a method of making the same, is described in detail below.

A substrate 12 was formed using a conventional spunlacing process and the substrate included 75% polyester fibers by weight and 25% rayon fibers by weight. The polyester fibers were Wellman Type D203, 1.5 dpf (1.7 dtex), fiber length 38 mm, commercially available from Wellman, Inc., Charlotte, N.C. The rayon fibers were Lenzing Type 8192 fibers, 1.5 dpf (1.7 dtex), fiber length 40 mm, commercially available from Lenzing AG, Lenzing, Austria.

The formed substrate 12 had a basis weight of 75 gsm and a thickness of 0.001 m. The Substrate Density (Sd, g/m$^3$) was determined by the formula, Sd (g/m$^3$)=Substrate Basis Weight (g/m$^2$)/Substrate Thickness (m). The calculated Substrate Density, Sd, for the formed substrate 12 was 7.5*10$^4$ g/m$^3$.

Average pore size of the substrate (Sp, microns) was determined utilizing a suitable apparatus such as a TRI/Autoporosimeter™, available from TRI, Princeton, N.J. The average pore size Sp was measured to be 62 microns.

The fibers respectively had the properties set forth below.

|  | Wellman Type D203 | Lenzing Type 8192 |
|---|---|---|
| Fiber Denier | 1.7 dTex | 1.7 dTex |
| Fiber Density | 1.37 * 10$^6$ g/m$^3$ | 1.51 * 10$^6$ g/m$^3$ |

An average fiber density was calculated according to the following formula:

$$Fd_{ave} (g/m^3)=[Fd_1*W_1]+[Fd_2*W_2]*10^6 \text{ microns/meter; where}$$

$Fd_1$=density of the first fiber;
$W_1$=weight percent of first fiber;
$Fd_2$=density of the second fiber; and
$W_2$=weight percent of the second fiber.

Thus, $Fd_{ave}$=[1.37*10$^6$*0.75]+[1.51*10$^6$*0.25]=1.405*10$^6$ g/m$^3$

In a similar fashion an average fiber size ($Fs_{ave}$) was calculated according to the following formula:

$$Fs_{ave} (dtex)=[Fs_1*W_1]+[Fs_2*W_2]; \text{ where}$$

$Fs_1$=size of the first fiber;
$W_1$=weight percent of first fiber;
$Fs_2$=size of the second fiber; and
$W_2$=weight percent of the second fiber.

Thus, $Fs_{ave}$(dtex)=[1.7*0.75]+[1.7*0.25]=1.7 dtex

An average fiber radius ($Fr_{ave}$) was then calculated according to the following formula:

$$Fr_{ave}(\text{microns}) = [((Fs_{ave}/10000\,m)/Fd_{ave})/3.14]^{1/2} * 10^6$$

Thus, $Fr_{ave}$ (microns)=$[((1.7/10000)/1.405*10^6)/3.14]^{1/2}*10^6$=6.2 microns The Tortuousity value (T) was then calculated according to the following formula:

$$T = Fr_{ave} * (Fd_{ave}/Sd - 1)/Sp$$

where
$Fr_{ave}$=Average Fiber Radius in microns (microns);
Fd=Average Fiber Density in grams per meter cubed (g/m$^3$);
Sd=Substrate Density (g/m$^3$); and
Sp=Average pore size of substrate in microns (microns).
Thus, T=$6.2*(1.405*10^6/7.5*10^4 - 1)/62$=1.77

The formed substrate 12 was unrolled from an unwind roll 102 and conveyed in a machine direction at a speed of 100 n/min. Cornstarch powder having particulate size of 5 microns and a moisture content of 8%, commercially available from Corn Products Corporation, Bedford Park, Ill., was applied to a top surface of the substrate 12 in an amount of 30 gsm. The substrate 12 including the cornstarch was conveyed to heated nip rolls 106a and 106b. Each of the nip rolls 106a and 106b had a diameter of 76 mm (3") and the gap setting (G) between the rolls was zero. The nips rolls 106a and 106b were each constructed from steel and had a smooth roll surface. The surface of each nip roll 106a and 106b was heated to a temperature of 170° C. (338° F.). A force was applied to the nip rolls 106a and 106b by means of a pair of air cylinders, each air cylinder having a pressure of 4.8 bar (70 psi) and an air cylinder diameter of 76 mm (3"). Thus the calculated nip force was 4.4 kN (990 lbs). The substrate 12 had a width of 76 mm (3") thus the compressive force applied to the substrate 12 was 0.6 kN/cm (330 lbs/in).

Absorbent System

The optional absorbent system 44 may comprise a single layer of material or may comprise multiple layers. In one embodiment, the absorbent system 44 is a blend or mixture of cellulosic fibers and superabsorbent disposed in and amongst fibers of that pulp.

It is possible that the absorbent system 44 could be integrated with the cover and/or barrier such that there is essentially only a single layer structure or a two layer structure including the function of the multiple layers described herein.

Cellulosic fibers that can be used in the absorbent system 44 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material. Some portion of the pulp may be chemically treated as discussed in U.S. Pat. No. 5,916,670 to improve the flexibility of the product. Flexibility of the material may also be improved by mechanically working the material or tenderizing the material. The absorbent system 44 can contain any superabsorbent polymer (SAP), which SAPs are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. In one embodiment of the invention, superabsorbent polymer particles for use in the present invention are crosslinked polyacrylates, such as the product offered by Sumitomo Seika Chemicals Co., Ltd. Of Osaka, Japan, under the designation of SA70N and products offered by Stockhausen Inc.

It is possible that the absorbent system 44 could be integrated with the cover and/or barrier such that there is essentially only a single layer structure or a two layer structure including the function of the multiple layers described herein.

Barrier Layer

Underlying the absorbent layer 44 is a barrier layer 50 comprising liquid-impervious film material so as to prevent liquid that is entrapped in the absorbent system 44 from egressing the sanitary liner and staining the wearer's undergarment. The barrier layer 50 is preferably made of polymeric film, although it may be made of liquid impervious, air-permeable material such as repellent-treated non-woven or micropore films or foams.

Positioning adhesive may be applied to a garment facing side of the barrier layer for securing the liner to the garment during use. The positioning adhesive may be covered with removable release paper so that the positioning adhesive is covered by the removable release paper prior to use.

The barrier layer may be breathable, i.e., permits vapor to transpire. Known materials for this purpose include non-woven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet. The cover layer 42 and the barrier layer 50 are joined along their marginal portions so as to form an enclosure or flange seal that maintains the absorbent layer 44 captive. The joint may be made by means of adhesives, heat-bonding, ultrasonic bonding, radio frequency sealing, mechanical crimping, and the like and combinations thereof.

Applications of the absorbent article according to the present invention for sanitary and other health-care uses can be accomplished by any sanitary protection, incontinence, medical and absorbent methods and techniques as are presently or prospectively known to those skilled in the art. Thus, it is intended that the present application cover the modifications and variations of this invention provided that they come within the scope of the appended claims and their equivalents.

We claim:

1. A method of making a cover material for an absorbent article comprising:
    providing a fibrous nonwoven substrate formed from a plurality of constituent fibers, said substrate having a tortuousity value in the range of about 0.8 to about 3.0;
    conveying said substrate in a machine direction to means for applying a skin care composition;
    applying a particulate skin care material to said substrate, said particulate skin care comprising a particulate material having a particle size in the range of about 1 micron to about 75 microns, wherein said particulate skin care material is not suspended in liquid or dissolved as a solution in liquid;
    conveying said substrate to means for applying a compressive force to said substrate;
    applying a compressive force to said substrate to impregnate said substrate with said particulate skin care material, wherein said compressive force is sufficient to impregnate said substrate during manufacturing yet permits the transfer of said particulate material to a body of a user during use of the absorbent article; and wherein a process temperature of said method is less than a melting temperature of said plurality of constituent fibers.

2. The method according to claim 1, wherein said skin care material has a moisture content of from about 3% to about 20%.

3. The method according to claim 1, wherein said compressive force is applied to said substrate by means of a pair of nip rolls having a zero gap setting.

4. The method according to claim 3, wherein said compressive force is applied to said substrate in an amount from about 0.1 kN/cm to about 1.2 kN/cm.

5. The method according to claim 4, wherein said compressive force is applied to said substrate in an amount from about 0.4 kN/cm to about 0.7 kN/cm.

6. The method according to claim 1, wherein said compressive force is applied to said substrate by a pair of nip rolls having a gap setting (G) as follows:

$0 < G < 0.5\ S_t$, where $S_t$ is a thickness of said substrate.

7. The method according to claim 6, wherein said gap setting (G) is as follows: $0.025\ mm < G < 0.25\ S_t$.

8. The method according to claim 1, further comprising:
simultaneously applying heat to said substrate with said application of said compressive force.

9. The method according to claim 8, wherein said heat is applied to said substrate by a pair of nip rolls having a surface temperature in the range of from about 25° C. to about 250° C.

10. The method according to claim 9, wherein said heat is applied to said by a pair of nip rolls having a surface temperature in the range of from about 35° C. to about 150° C.

11. The method according to claim 1, wherein said fibrous nonwoven substrate is free from any immobilizing agents for securing said particulate skin care material to said substrate.

12. The method according to claim 1, wherein said particulate material has a particle size in the range of about 5 microns to about 30 microns.

13. The method according to claim 1, wherein said fibrous nonwoven substrate has a tortuosity value in the range of about 1.0 to about 1.8.

14. The method according to claim 1, wherein skin care material has a moisture content of from about 8% to about 14%.

15. The method according to claim 1, wherein said fibrous nonwoven substrate has an average pore size in the range of about 40 microns to about 200 microns.

16. The method according to claim 1, wherein said fibrous nonwoven substrate has an average pore size in the range of about 60 microns to about 150 microns.

17. The method according to claim 1, wherein said fibrous nonwoven substrate comprises a plurality of fibers, each of said fibers having a fiber density of about $5.0*10^5$ g/m$^3$ to about $2.0*10^6$ g/m$^3$.

18. The method according to claim 17, wherein each of said fibers has a fiber density of about $9.0*10^5$ g/m$^3$ to about $1.5*10^6$ g/m$^3$.

19. The method according to claim 1, wherein said fibrous nonwoven substrate consists essentially of a plurality of fibers, each of said fibers having a fiber size in the range of about 1.0 dtex to about 7.8 dtex.

20. The method according to claim 19, wherein each of said fibers has fiber size in the range of about 1.7 dtex to about 5.6 dtex.

21. The method according to claim 1, wherein said fibrous nonwoven substrate comprises a plurality of fibers, each of said fibers having a fiber radius in the range of about 3 microns to about 25 microns.

22. The method according to claim 21, wherein each of said fibers has a fiber radius in the range of about 5 microns to about 12 microns.

23. The method according to claim 1, wherein said fibrous nonwoven substrate has a basis weight in the range of about 40 gsm to about 200 gsm.

24. The method according to claim 23, wherein said fibrous nonwoven substrate has a basis weight in the range of about 60 gsm to about 150 gsm.

25. The method according to claim 1, wherein said substrate has a density in the range of about $1.0*10^4$ g/m$^3$ to about $3.0*10^5$ g/m$^3$.

26. The method according to claim 25, wherein said substrate has a density in the range of about $5.0*10^4$ g/m$^3$ to about $1.0*10^5$ g/m$^3$.

27. The method according to claim 1, wherein said skin care material is present in an amount from about 1 gsm to about 50 gsm.

28. The method according to claim 27, wherein said skin care material is present in an amount from about 5 gsm to about 20 gsm.

29. The method according to claim 1, wherein said substrate is conveyed at a speed from about 7.5 m/min to about 500 m/min.

30. The method according to claim 29, wherein said substrate is conveyed at a speed from about 100 m/min to about 350 m/min.

* * * * *